(12) United States Patent
Funkhouser et al.

(10) Patent No.: US 7,700,525 B2
(45) Date of Patent: *Apr. 20, 2010

(54) ORTHOESTER-BASED SURFACTANTS AND ASSOCIATED METHODS

(75) Inventors: Gary P. Funkhouser, Duncan, OK (US); Rajesh K. Saini, Duncan, OK (US)

(73) Assignee: Halliburton Energy Services, Inc., Duncan, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 12/565,392

(22) Filed: Sep. 23, 2009

(65) Prior Publication Data

US 2010/0016184 A1    Jan. 21, 2010

Related U.S. Application Data

(62) Division of application No. 11/232,504, filed on Sep. 22, 2005, now abandoned.

(51) Int. Cl.
C09K 8/60    (2006.01)

(52) U.S. Cl. .............. 507/246; 507/261; 166/278; 166/279; 166/305.1

(58) Field of Classification Search ............... 507/261, 507/246; 166/278, 279, 305.1
See application file for complete search history.

(56) References Cited

U.S. PATENT DOCUMENTS

| | | | |
|---|---|---|---|
| 2,238,671 A | 4/1941 | Woodhouse |
| 2,703,316 A | 3/1955 | Palmer |
| 3,173,484 A | 3/1965 | Huitt et al. |
| 3,195,635 A | 7/1965 | Fast |
| 3,272,650 A | 9/1966 | MacVittie |
| 3,302,719 A | 2/1967 | Fischer |
| 3,364,995 A | 1/1968 | Atkins et al. |
| 3,366,178 A | 1/1968 | Malone et al. |
| 3,455,390 A | 7/1969 | Gallus |
| 3,784,585 A | 1/1974 | Schmitt et al. |
| 3,819,525 A | 6/1974 | Hattenbrun |
| 3,828,854 A | 8/1974 | Templeton et al. |
| 3,836,465 A | 9/1974 | Rhudy et al. |
| 3,868,998 A | 3/1975 | Lybarger et al. |
| 3,912,692 A | 10/1975 | Casey et al. |
| 3,948,672 A | 4/1976 | Harnsberger |
| 3,955,993 A | 5/1976 | Curtice |
| 3,960,736 A | 6/1976 | Free et al. |
| 3,968,840 A | 7/1976 | Tate |
| 3,986,355 A | 10/1976 | Klaeger |
| 3,998,272 A | 12/1976 | Maly |
| 3,998,744 A | 12/1976 | Arnold et al. |
| 4,010,071 A | 3/1977 | Colegrove |
| 4,068,718 A | 1/1978 | Cooke, Jr. et al. |
| 4,169,798 A | 10/1979 | DeMartino |
| 4,172,066 A | 10/1979 | Zweigle et al. |
| 4,261,421 A | 4/1981 | Watanabe |
| 4,265,673 A | 5/1981 | Pace et al. |
| 4,299,825 A | 11/1981 | Lee |
| 4,387,769 A | 6/1983 | Erbstoesser et al. |
| 4,460,052 A | 7/1984 | Gockel |
| 4,470,915 A | 9/1984 | Conway |
| 4,498,995 A | 2/1985 | Gockel |
| 4,502,540 A | 3/1985 | Byham |
| 4,506,734 A | 3/1985 | Nolte |
| 4,517,102 A | 5/1985 | Salathiel |
| 4,521,316 A | 6/1985 | Sikorski |
| 4,526,695 A | 7/1985 | Erbstoesser et al. |
| 4,632,876 A | 12/1986 | Laird et al. |
| 4,694,905 A | 9/1987 | Armbruster |
| 4,715,967 A | 12/1987 | Bellis |
| 4,716,964 A | 1/1988 | Erbstoesser et al. |
| 4,767,706 A | 8/1988 | Levesque |
| 4,772,346 A | 9/1988 | Anderson et al. |
| 4,785,884 A | 11/1988 | Armbruster |
| 4,793,416 A | 12/1988 | Mitchell |
| 4,797,262 A | 1/1989 | Dewitz |
| 4,809,783 A | 3/1989 | Hollenbeck et al. |
| 4,817,721 A | 4/1989 | Pober |
| 4,822,500 A | 4/1989 | Dobson, Jr. et al. |
| 4,829,100 A | 5/1989 | Murphey et al. |

(Continued)

FOREIGN PATENT DOCUMENTS

EP    0 510 762    10/1992

(Continued)

OTHER PUBLICATIONS

Simmons, et al., *Poly(phenyllactide): Synthesis, Characterization, and Hydrolytic Degradation*, Biomacromolecules, vol. 2, No. 2, 2001 (pp. 658-663).

(Continued)

*Primary Examiner*—Randy Gulakowski
*Assistant Examiner*—Alicia M Toscano
(74) *Attorney, Agent, or Firm*—Robert A. Kent

(57) ABSTRACT

Provided are treatment fluids that comprise a base fluid and an orthoester-based surfactant. In some instances, the treatment fluid may have a pH of about 8.5 or greater. Also provided are emulsified treatment fluids that comprise an oleaginous phase, an aqueous phase having a pH of about 8.5 or greater, and an orthoester-based surfactant. Methods of using the treatment fluid and methods of facilitating flow through a conduit also are provided.

18 Claims, No Drawings

U.S. PATENT DOCUMENTS

| | | |
|---|---|---|
| 4,836,940 A | 6/1989 | Alexander |
| 4,843,118 A | 6/1989 | Lai et al. |
| 4,848,467 A | 7/1989 | Cantu et al. |
| 4,863,980 A | 9/1989 | Cowan et al. |
| 4,886,354 A | 12/1989 | Welch et al. |
| 4,894,231 A | 1/1990 | Moreau et al. |
| 4,957,165 A | 9/1990 | Cantu et al. |
| 4,961,466 A | 10/1990 | Himes et al. |
| 4,986,353 A | 1/1991 | Clark et al. |
| 4,986,354 A | 1/1991 | Cantu et al. |
| 4,986,355 A | 1/1991 | Casad et al. |
| 5,034,139 A | 7/1991 | Reid et al. |
| 5,082,056 A | 1/1992 | Tackett, Jr. |
| 5,142,023 A | 8/1992 | Gruber et al. |
| 5,152,781 A | 10/1992 | Tang et al. |
| 5,161,615 A | 11/1992 | Hutchins et al. |
| 5,203,834 A | 4/1993 | Hutchins et al. |
| 5,213,446 A | 5/1993 | Dovan |
| 5,216,050 A | 6/1993 | Sinclair |
| 5,247,059 A | 9/1993 | Gruber et al. |
| 5,249,628 A | 10/1993 | Surjaatmadja |
| 5,251,697 A | 10/1993 | Shuler |
| 5,295,542 A | 3/1994 | Cole et al. |
| 5,304,620 A | 4/1994 | Holtmyer et al. |
| 5,314,031 A | 5/1994 | Hale et al. |
| 5,325,923 A | 7/1994 | Surjaatmadja et al. |
| 5,330,005 A | 7/1994 | Card et al. |
| 5,359,026 A | 10/1994 | Gruber |
| 5,360,068 A | 11/1994 | Sprunt et al. |
| 5,363,916 A | 11/1994 | Himes et al. |
| 5,373,901 A | 12/1994 | Norman et al. |
| 5,386,874 A | 2/1995 | Laramay et al. |
| 5,396,957 A | 3/1995 | Surjaatmadja et al. |
| 5,402,846 A | 4/1995 | Jennings, Jr. et al. |
| 5,439,055 A | 8/1995 | Card et al. |
| 5,460,226 A | 10/1995 | Lawton et al. |
| 5,464,060 A | 11/1995 | Hale et al. |
| 5,475,080 A | 12/1995 | Gruber et al. |
| 5,484,881 A | 1/1996 | Gruber et al. |
| 5,487,897 A | 1/1996 | Polson et al. |
| 5,492,177 A | 2/1996 | Yeh et al. |
| 5,496,557 A | 3/1996 | Feijen et al. |
| 5,497,830 A | 3/1996 | Boles et al. |
| 5,499,678 A | 3/1996 | Surjaatmadja et al. |
| 5,501,276 A | 3/1996 | Weaver et al. |
| 5,505,787 A | 4/1996 | Yamaguchi |
| 5,512,071 A | 4/1996 | Yam et al. |
| 5,536,807 A | 7/1996 | Gruber et al. |
| 5,555,936 A | 9/1996 | Pirri et al. |
| 5,591,700 A | 1/1997 | Harris et al. |
| 5,594,095 A | 1/1997 | Gruber et al. |
| 5,602,083 A | 2/1997 | Gabrysch et al. |
| 5,604,186 A | 2/1997 | Hunt et al. |
| 5,607,905 A | 3/1997 | Dobson, Jr. et al. |
| 5,613,558 A | 3/1997 | Dillenbeck |
| 5,670,473 A | 9/1997 | Scepanski |
| 5,697,440 A | 12/1997 | Weaver et al. |
| 5,698,322 A | 12/1997 | Tsai et al. |
| 5,723,416 A | 3/1998 | Liao |
| 5,765,642 A | 6/1998 | Surjaatmadja |
| 5,783,527 A | 7/1998 | Dobson, Jr. et al. |
| 5,791,415 A | 8/1998 | Nguyen et al. |
| 5,799,734 A | 9/1998 | Normal et al. |
| 5,833,000 A | 11/1998 | Weaver et al. |
| 5,849,401 A | 12/1998 | El-Afandi et al. |
| 5,853,048 A | 12/1998 | Weaver et al. |
| 5,893,416 A | 4/1999 | Read |
| 5,908,073 A | 6/1999 | Nguyen et al. |
| 5,916,849 A | 6/1999 | House |
| 5,924,488 A | 7/1999 | Nguyen et al. |
| 5,964,291 A | 10/1999 | Bourne et al. |
| 5,977,030 A | 11/1999 | House |
| 5,979,557 A | 11/1999 | Card et al. |
| 5,996,693 A | 12/1999 | Heathman |
| 6,004,400 A | 12/1999 | Bishop et al. |
| 6,024,170 A | 2/2000 | McCabe et al. |
| 6,028,113 A | 2/2000 | Scepanski |
| 6,047,772 A | 4/2000 | Weaver et al. |
| 6,110,875 A | 8/2000 | Tjon-Joe-Pin et al. |
| 6,114,410 A | 9/2000 | Betzold |
| 6,123,159 A | 9/2000 | Brookey et al. |
| 6,123,965 A | 9/2000 | Jacob et al. |
| 6,131,661 A | 10/2000 | Conner et al. |
| 6,135,987 A | 10/2000 | Tsai et al. |
| 6,143,698 A | 11/2000 | Murphey et al. |
| 6,148,917 A | 11/2000 | Brookey et al. |
| 6,162,766 A | 12/2000 | Muir et al. |
| 6,169,058 B1 | 1/2001 | Le et al. |
| 6,172,011 B1 | 1/2001 | Card et al. |
| 6,189,615 B1 | 2/2001 | Sydansk |
| 6,202,751 B1 | 3/2001 | Chatterji et al. |
| 6,209,643 B1 | 4/2001 | Nguyen et al. |
| 6,209,646 B1 | 4/2001 | Reddy et al. |
| 6,214,773 B1 | 4/2001 | Harris et al. |
| 6,242,390 B1 | 6/2001 | Mitchell et al. |
| 6,260,622 B1 | 7/2001 | Blok et al. |
| 6,291,013 B1 | 9/2001 | Gibson et al. |
| 6,300,286 B1 | 10/2001 | Dobson, Jr. et al. |
| 6,302,209 B1 | 10/2001 | Thompson et al. |
| 6,308,788 B1 | 10/2001 | Patel et al. |
| 6,311,773 B1 | 11/2001 | Todd et al. |
| 6,323,307 B1 | 11/2001 | Bigg et al. |
| 6,326,458 B1 | 12/2001 | Gruber et al. |
| 6,328,105 B1 | 12/2001 | Betzold |
| 6,330,917 B2 | 12/2001 | Chatterji et al. |
| 6,357,527 B1 | 3/2002 | Norman et al. |
| 6,364,945 B1 | 4/2002 | Chatterji et al. |
| 6,380,138 B1 | 4/2002 | Ischy et al. |
| 6,387,986 B1 | 5/2002 | Moradi-Araghi et al. |
| 6,390,195 B1 | 5/2002 | Nguyen et al. |
| 6,394,185 B1 | 5/2002 | Constien |
| 6,422,314 B1 | 7/2002 | Todd et al. |
| 6,422,326 B1 | 7/2002 | Brookey et al. |
| 6,432,155 B1 | 8/2002 | Swazey et al. |
| 6,454,003 B1 | 9/2002 | Chang et al. |
| 6,485,947 B1 | 11/2002 | Rajgarhia et al. |
| 6,488,763 B2 | 12/2002 | Brothers et al. |
| 6,494,263 B2 | 12/2002 | Todd |
| 6,508,305 B1 | 1/2003 | Brannon et al. |
| 6,509,301 B1 | 1/2003 | Vollmer et al. |
| 6,527,051 B1 | 3/2003 | Reddy et al. |
| 6,534,449 B1 | 3/2003 | Gilmour et al. |
| 6,554,071 B1 | 4/2003 | Reddy et al. |
| 6,566,310 B2 | 5/2003 | Chan |
| 6,569,814 B1 | 5/2003 | Brady et al. |
| 6,578,630 B2 | 6/2003 | Simpson et al. |
| 6,599,863 B1 | 7/2003 | Palmer et al. |
| 6,667,279 B1 | 12/2003 | Hessert et al. |
| 6,669,771 B2 | 12/2003 | Tokiwa et al. |
| 6,681,856 B1 | 1/2004 | Chatterji et al. |
| 6,686,328 B1 | 2/2004 | Binder |
| 6,691,780 B2 | 2/2004 | Nguyen et al. |
| 6,702,023 B1 | 3/2004 | Harris et al. |
| 6,710,019 B1 | 3/2004 | Sawdon et al. |
| 6,716,797 B2 | 4/2004 | Brookey |
| 6,737,385 B2 | 5/2004 | Todd et al. |
| 6,761,218 B2 | 7/2004 | Nguyen et al. |
| 6,763,888 B1 | 7/2004 | Harris et al. |
| 6,764,981 B1 | 7/2004 | Eoff et al. |
| 6,776,238 B2 | 8/2004 | Dusterhoft et al. |
| 6,793,018 B2 | 9/2004 | Dawson et al. |
| 6,793,730 B2 | 9/2004 | Reddy et al. |
| 6,806,235 B1 | 10/2004 | Mueller et al. |
| 6,817,414 B2 | 11/2004 | Lee |

| | | |
|---|---|---|
| 6,818,594 B1 | 11/2004 | Freeman et al. |
| 6,837,309 B2 | 1/2005 | Boney et al. |
| 6,840,318 B2 | 1/2005 | Lee et al. |
| 6,852,173 B2 | 2/2005 | Banerjee et al. |
| 6,861,394 B2 | 3/2005 | Ballard et al. |
| 6,883,608 B2 | 4/2005 | Parlar et al. |
| 6,886,635 B2 | 5/2005 | Hossaini et al. |
| 6,896,058 B2 | 5/2005 | Munoz, Jr. et al. |
| 6,904,971 B2 | 6/2005 | Brothers et al. |
| 6,949,491 B2 | 9/2005 | Cooke, Jr. |
| 6,959,767 B2 | 11/2005 | Horton et al. |
| 6,978,838 B2 | 12/2005 | Parlar et al. |
| 6,981,552 B2 | 1/2006 | Reddy et al. |
| 6,983,801 B2 | 1/2006 | Dawson et al. |
| 6,987,083 B2 | 1/2006 | Phillippi et al. |
| 6,997,259 B2 | 2/2006 | Nguyen |
| 7,000,701 B2 | 2/2006 | Todd et al. |
| 7,007,752 B2 | 3/2006 | Reddy et al. |
| 7,021,377 B2 | 4/2006 | Todd et al. |
| 7,032,663 B2 | 4/2006 | Nguyen |
| 7,036,586 B2 | 5/2006 | Roddy et al. |
| 7,036,587 B2 | 5/2006 | Munoz, Jr. et al. |
| 7,044,220 B2 | 5/2006 | Nguyen et al. |
| 7,044,224 B2 | 5/2006 | Nguyen |
| 7,049,272 B2 | 5/2006 | Sinclair et al. |
| 7,063,151 B2 | 6/2006 | Nguyen et al. |
| 7,066,258 B2 | 6/2006 | Justus et al. |
| 7,066,260 B2 | 6/2006 | Sullivan et al. |
| 7,069,994 B2 | 7/2006 | Cooke, Jr. |
| 7,080,688 B2 | 7/2006 | Todd et al. |
| 7,093,664 B2 | 8/2006 | Todd et al. |
| 7,096,947 B2 | 8/2006 | Todd et al. |
| 7,101,829 B2 | 9/2006 | Guichard et al. |
| 7,131,491 B2 | 11/2006 | Blauch et al. |
| 7,132,389 B2 | 11/2006 | Lee |
| 7,140,438 B2 | 11/2006 | Frost et al. |
| 7,147,067 B2 | 12/2006 | Getzlaf et al. |
| 7,151,077 B2 | 12/2006 | Prudhomme et al. |
| 7,153,902 B2 | 12/2006 | Altes et al. |
| 7,156,174 B2 | 1/2007 | Roddy et al. |
| 7,165,617 B2 | 1/2007 | Lord et al. |
| 7,166,560 B2 | 1/2007 | Still et al. |
| 7,168,489 B2 | 1/2007 | Frost et al. |
| 7,172,022 B2 | 2/2007 | Reddy et al. |
| 7,178,596 B2 | 2/2007 | Blauch et al. |
| 7,195,068 B2 | 3/2007 | Todd |
| 7,204,312 B2 | 4/2007 | Roddy et al. |
| 7,205,264 B2 | 4/2007 | Boles |
| 7,216,705 B2 | 5/2007 | Saini et al. |
| 7,219,731 B2 | 5/2007 | Sullivan |
| 7,228,904 B2 | 6/2007 | Todd et al. |
| 7,261,156 B2 | 8/2007 | Nguyen et al. |
| 7,264,051 B2 | 9/2007 | Nguyen et al. |
| 7,265,079 B2 | 9/2007 | Wilbert et al. |
| 7,267,170 B2 | 9/2007 | Mang et al. |
| 7,276,466 B2 | 10/2007 | Todd et al. |
| 7,299,869 B2 | 11/2007 | Kalman |
| 7,303,014 B2 | 12/2007 | Reddy et al. |
| 7,306,037 B2 | 12/2007 | Nguyen et al. |
| 7,322,412 B2 | 1/2008 | Badalamenti et al. |
| 2001/0016562 A1 | 8/2001 | Muir et al. |
| 2002/0119169 A1 | 8/2002 | Angel et al. |
| 2003/0054962 A1 | 3/2003 | England et al. |
| 2003/0130133 A1 | 7/2003 | Vollmer |
| 2003/0147965 A1 | 8/2003 | Basset et al. |
| 2003/0230407 A1 | 12/2003 | Vijn et al. |
| 2004/0014606 A1 | 1/2004 | Parlar et al. |
| 2004/0039235 A1 | 2/2004 | Bergstrom et al. |
| 2004/0070093 A1 | 4/2004 | Mathiowitz et al. |
| 2004/0099416 A1 | 5/2004 | Vijn et al. |
| 2004/0102330 A1 | 5/2004 | Zhou et al. |
| 2004/0138068 A1 | 7/2004 | Rimmer et al. |
| 2004/0146550 A1 * | 7/2004 | Ng et al. .................. 424/450 |
| 2004/0170836 A1 | 9/2004 | Bond et al. |
| 2004/0214725 A1 | 10/2004 | Moss |
| 2004/0231845 A1 | 11/2004 | Cooke, Jr. |
| 2005/0028976 A1 | 2/2005 | Nguyen |
| 2005/0034861 A1 | 2/2005 | Saini et al. |
| 2005/0045328 A1 | 3/2005 | Frost et al. |
| 2005/0059556 A1 | 3/2005 | Munoz, Jr. et al. |
| 2005/0059557 A1 | 3/2005 | Todd et al. |
| 2005/0059558 A1 | 3/2005 | Blauch et al. |
| 2005/0126785 A1 | 6/2005 | Todd et al. |
| 2005/0130848 A1 | 6/2005 | Todd et al. |
| 2005/0183741 A1 | 8/2005 | Surjaatmadja et al. |
| 2005/0205266 A1 | 9/2005 | Todd et al. |
| 2005/0272613 A1 | 12/2005 | Cooke, Jr. |
| 2005/0277554 A1 | 12/2005 | Blauch et al. |
| 2006/0016596 A1 | 1/2006 | Pauls et al. |
| 2006/0032633 A1 | 2/2006 | Nguyen |
| 2006/0046938 A1 | 3/2006 | Harris et al. |
| 2006/0065397 A1 | 3/2006 | Nguyen et al. |
| 2006/0105917 A1 | 5/2006 | Munoz, Jr. et al. |
| 2006/0105918 A1 | 5/2006 | Munoz, Jr. et al. |
| 2006/0169182 A1 | 8/2006 | Todd et al. |
| 2006/0169450 A1 | 8/2006 | Mang et al. |
| 2006/0172891 A1 | 8/2006 | Gewehr et al. |
| 2006/0172893 A1 | 8/2006 | Todd et al. |
| 2006/0172894 A1 | 8/2006 | Mang et al. |
| 2006/0172895 A1 | 8/2006 | Mang et al. |
| 2006/0185848 A1 | 8/2006 | Surjaatmadja et al. |
| 2006/0276345 A1 | 12/2006 | Todd et al. |
| 2007/0298977 A1 | 12/2007 | Mang et al. |
| 2008/0009423 A1 | 1/2008 | Mang et al. |

FOREIGN PATENT DOCUMENTS

| | | |
|---|---|---|
| EP | 0 879 935 | 2/1999 |
| EP | 1 413 710 | 4/2004 |
| GB | 2 412 389 | 3/2004 |
| WO | WO 93/15127 | 8/1993 |
| WO | WO 94/07949 | 4/1994 |
| WO | WO 94/08078 | 4/1994 |
| WO | WO 94/08090 | 4/1994 |
| WO | WO 95/09879 | 4/1995 |
| WO | WO 97/11845 | 4/1997 |
| WO | WO 99/27229 | 6/1999 |
| WO | WO 00/57022 | 9/2000 |
| WO | WO 01/02698 | 1/2001 |
| WO | WO 01/87797 | 11/2001 |
| WO | WO 01/94744 | 12/2001 |
| WO | WO 02/55843 | 1/2002 |
| WO | WO 02/12674 | 2/2002 |
| WO | WO 03/027431 | 4/2003 |
| WO | WO 2004/007905 | 1/2004 |
| WO | WO 2004/037946 | 5/2004 |
| WO | WO 2004/038176 | 5/2004 |

OTHER PUBLICATIONS

Yin, et al., *Preparation and Characterization of Substituted Polylactides*, American Chemical Society, vol. 32, No, 23, 1999 (pp. 7711-7718).

Yin, et al., *Synthesis and Properties of Polymers Derived form Substituted Lactic Acids*, American Chemical Society, Ch. 12, 2001 (pp. 147-159).

Cantu, et al, *Laboratory and Field Evaluation of a Combined Fluid-Loss-Control Additive and Gel Breaker for Fracturing Fluids*, SPE 18211, Society of Petroleum Engineers, 1990.

Love, et al, *Selectively Placing Many Fractures in Openhole Horizontal Wells Improves Production*, SPE 50422, Society of Petroleum Engineers, 1998.

McDaniel, et al, *Evolving New Stimulation Process Proves Highly Effective in Level 1 Dual-Lateral Completion*, SPE 78697, Society of Petroleum Engineers, 2002.

Albertsson, et al, *Aliphatic Polyesters: Systhesis, Properties and Applications*, Advances in Polymer Science, vol. 157, Degradable Aliphatic Polyesters, 2002.

Dechy-Cabaret, et al, *Controlled Ring-Opening Polymerization of Lactide and Glycolide*, American Chemical Society, Chemical Reviews, A-Z, AA-AD, received 2004.

Funkhouser, et al, *Synthetic Polymer Fracturing Fluid for High-Temperature Applications*, SPE 80236, Society of Petroleum Engineers, 2003.

*Chelating Agents*, Encyclopedia of Chemical Technology, vol. 5 (764-795), 2001.

Vichaibun, et al, *A New Assay for the Enzymatic Degradation of Polylactic Acid, Short Report*, ScienceAsia, vol. 29, 2003 (pp. 297-300).

Halliburton, *SurgiFrac<sup>SM</sup> Service, A Quick and Cost-Effective Method to Help Boost Production From Openhole Horizontal Completions*, Halliburton Communications, HO3297, 2002.

Halliburton, *Cobra Frac<sup>SM</sup> Service, Coiled Tubing Fracturing—Cost-Effective Method for Stimulating Untapped Reserves*, HO2319R, Halliburton Energy Services, 2000.

Halliburton, *CobraJet Frac<sup>SM</sup> Service, Cost-effective Technology That Can Help Reduce Cost Per BOE Produced, Shorten Cycle Time and Reduce Capex*, Halliburton Communications, Apr. 2003.

Y. Chiang et al., *Hydrolysis Of Ortho Esters; Further Investigation Of The Factors Which Control The Rate-Determining Step*, Engineering Information, Inc. NY, NY, vol. 105, No. 23 (XP-002322842), Nov. 16, 1983.

M. Ahmad, et al., *Ortho Ester Hydrolysis: Direct Evidence For A Three-Stage Reaction Mechanism*, Engineering Information, Inc. NY, NY, vol. 101, No. 10 (XP-002322843), May 9, 1979.

Skrabal et al, *The Hydrolysis Rate of Orthoformic Acid Ethyl Ether*, Chemical Institute of the University of Graz, Jan. 13, 1921, pp. 1-38.

Heller, et al., *Poly(ortho esters)—From Concept To Reality*, Biomacromolecules, vol. 5, No. 5, 2004 (pp. 1625-1632), May 9, 1979.

Schwach-Abdellaoui, et al., *Hydrolysis and Erosion Studies of Autocatalyzed Poly(ortho esters) Containing Lactoyl-Lactyl Acid Dimers*, American Chemical Society, vol. 32, No. 2, 1999 (pp. 301-307).

Ng, et al., *Synthesis and Erosion Studies of Self-Catalyzed Poly(ortho ester)s*, American Chemical Society, vol. 30, No. 4, 1997 (pp. 770-772).

Ng, et al., *Development Of A Poly(ortho ester) prototype With A Latent Acid In The Polymer Backbone For 5-fluorouracil Delivery*, Journal of Controlled Release 65 (2000), (pp. 367-374).

Rothen-Weinhold, et al., *Release of BSA from poly(ortho ester) extruded thin strands*, Journal of Controlled Release 71, 2001, (pp. 31-37).

Heller, et al., *Poly(ortho ester)s—their development and some recent applications*, European Journal of Pharmaceutics and Biopharmaceutics, 50, 2000, (pp. 121-128).

Heller, et al., *Poly(ortho esters); synthesis, characterization, properties and uses*, Advanced Drug Delivery Reviews, 54, 2002, (pp. 1015-1039).

Heller, et al., *Poly(ortho esters) For The Pulsed And Continuous Delivery of Peptides And Proteins*, Controlled Release and Biomedical Polymers Department, SRI International, (pp. 39-46), 1995.

Zignani, et al., *Subconjunctival biocompatibility of a viscous bioerodable poly(ortho ester)*, J. Biomed Mater Res, 39, 1998, pp. 277-285.

Toncheva, et al., *Use of Block Copolymers of Poly(Ortho Esters) and Poly (Ethylene Glycol)*, Journal of Drug Targeting, 2003, vol. 11(6), pp. 345-353.

Schwach-Abdellaoui, et al., *Control of Molecular Weight For Auto-Catalyzed Poly(ortho ester) Obtained by Polycondensation Reaction*, International Journal of Polymer Anal. Charact., 7: 145-161, 2002, pp. 145-161.

Heller, et al., *Release of Norethindrone from Poly(Ortho Esters)*, Polymer Engineering and Science, Mid-Aug. 1981, vol. 21, No. 11 (pp. 727-731).

Cordes, et al., *Mechanism and Catalysis for Hydrolysis of Acetals, Ketals, and Other Esters*, Department of Chemistry, Indiana University, Bloomington, Indiana, Chemical Reviews, 1974, vol. 74, No. 5, pp. 581-603.

Todd, et al., *A Chemcial "TRIGGER" Useful for Oilfield Applications*, Society of Petroleum Engineers, Inc., SPE 92709, Feb. 4, 2005.

Kiyoshi Matsuyama et al, *Environmentally Bnign Formation of Polymeric Microspheres by Rapid Expansion of Supercritical Carbon Dioxide Solution With a Nonsolvent*, Environ Sci Technol 2001, 35, 4149-4155.

Office Action for U.S. Appl. No. 11/232,504 dated Sep. 8, 2008.
Office Action for U.S. Appl. No. 11/232,504 dated Mar. 2, 2009.
Office Action for U.S. Appl. No. 11/128,060 dated May 14, 2009.
Office Action for U.S. Appl. No. 11/232,687 dated Mar. 24, 2009.

* cited by examiner

ORTHOESTER-BASED SURFACTANTS AND ASSOCIATED METHODS

CROSS-REFERENCE TO RELATED APPLICATIONS

This application is a divisional application of U.S. patent application Ser. No. 11/232,504 entitled "Orthoester-Based Surfactants and Associated Methods," filed on Sep. 22, 2005 now abandoned by Funkhouser et al., the entirety of which is herein incorporated by reference for all purposes. This application is also related to U.S. patent application Ser. No. 11/232,687 and U.S. Patent Application Publication No. 2007/0066493 entitled "Orthoester-Based Surfactants and Associated Methods," filed on Sep. 22, 2005 by Funkhouser et al., the entirety of which is herein incorporated by reference for all purposes.

BACKGROUND

The present invention relates to orthoester-based surfactants. More particularly, the present invention relates to treatment fluids comprising orthoester-based surfactants and associated methods.

Surfactants may be used in a variety of applications. Such applications may be above or below ground, for example, in a subterranean formation penetrated by a well bore. Where used in above-ground applications, surfactants may be used, for example, to emulsify an oleaginous fluid (e.g., a heavy oil) to facilitate transport in a pipeline. Surfactants also may be used in subterranean applications, for example, in drilling operations, stimulation treatments (e.g., fracturing treatments), well bore cleanups, viscous sweeps, and completion operations (e.g., sand control treatments, gravel packing). In these applications, the surfactants may be used for a number of purposes, including as emulsifying agents, non-emulsifying agents, foaming agents, defoaming agents, dispersants, wetting agents, and the like.

While a variety of surfactants have been used in subterranean applications, problems have been associated with their use. For instance, certain surfactants used heretofore may have undesirable environmental characteristics and/or may be limited by strict environmental regulations in certain areas of the world. Thus, degradable surfactants have been used to reduce the potential for bioaccumulation and/or persistence of such surfactants in the environment. Currently available degradable surfactants, such as esters, amides, and acetals, have characteristics that may limit their usefulness in subterranean applications. For instance, esters and amides may not degrade as desired in conditions that may be encountered downhole. Further, degradation of esters and amides is slowest at pHs encountered in the subterranean environment, and thus may result in unacceptably long persistence times. Likewise, problems also may be encountered with the use of acetals in subterranean applications. While acetals are usually stable at high pH values (e.g., > about 6), low pH values (e.g., about 1-4) may be required for their degradation to occur at desirable rates. This typically requires exposure of the surfactant to an acid to facilitate the degradation thereof after introduction into the subterranean formation, which may add undesired expense and complexity to the subterranean application.

SUMMARY

The present invention relates to orthoester-based surfactants. More particularly, the present invention relates to treatment fluids comprising orthoester-based surfactants and associated methods. As used herein, the term "orthoester-based surfactant" refers to amphiphilic compounds that contain one or more orthoester functional groups.

In one embodiment, the present invention provides a method that comprises: providing a treatment fluid comprising a base fluid and an orthoester-based surfactant; and introducing the treatment fluid into a subterranean formation.

Another embodiment of the present invention provides a method comprising: providing an emulsified treatment fluid comprising an oleaginous phase, an aqueous phase having a pH of about 8.5 or greater, and an orthoester-based surfactant; and introducing the emulsified treatment fluid into a subterranean formation.

Another embodiment of the present invention provides a method of facilitating flow through a conduit comprising: providing an emulsified treatment fluid comprising an orthoester-based surfactant, an oleaginous phase, and an aqueous phase having a pH of about 8.5 or greater; flowing the emulsified treatment fluid through the conduit; and reducing the pH of the aqueous phase so as to facilitate degradation of at least a portion of the orthoester-based surfactant, thereby facilitating separation of the oleaginous phase and the aqueous phase.

Yet another embodiment of the present invention provides a method of synthesizing an orthoester-based surfactant comprising: providing a diketene acetal or a multiketene acetal, and reacting the diketene acetal or the multiketene acetal with one or more hydrophobic alcohols and one or more hydrophilic alcohols.

The features and advantages of the present invention will be readily apparent to those skilled in the art upon a reading of the description of the preferred embodiments that follows.

DESCRIPTION OF PREFERRED EMBODIMENTS

The present invention relates to orthoester-based surfactants. More particularly, the present invention relates to treatment fluids comprising orthoester-based surfactants and associated methods. These treatment fluids may be suitable for use in a variety of subterranean applications, including, but not limited to, drilling operations, stimulation treatments (e.g., fracturing treatments), well bore cleanups, viscous sweeps, and completion operations (e.g., sand control treatments, gravel packing). These treatment fluids also may be used above ground, for example, to facilitate the transport of an oleaginous fluid. As used herein, the term "treatment," or "treating," refers to any operation that uses a fluid in conjunction with a desired function and/or for a desired purpose. The term "treatment," or "treating," does not imply any particular action by the fluid.

I. Treatment Fluids of the Present Invention

The treatment fluids of the present invention generally comprise a base fluid and an orthoester-based surfactant. These treatment fluids may include aqueous fluids, aqueous gels, viscoelastic surfactant gels, oil gels, foamed gels, and emulsions (e.g., water-in-oil or oil-in-water). The orthoester-based surfactants included in these treatment fluids are generally degradable, wherein the degradation of the orthoester linkages therein generally should result in the destruction, or reduction, of the surfactant's surface activity. The rates of the orthoester-based surfactant's degradation should increase with decreasing pH and increasing temperature. However, these orthoester-based surfactants generally are stable at a pH of about 8.5 or greater. Among other things, the orthoester-based surfactants may be included in the treatment fluids of the present invention for any of a number of purposes, including as emulsifying agents, non-emulsifying agents, foaming agents, defoaming agents, dispersants, wetting agents, combinations thereof, and the like.

The base fluids included in the treatment fluids of the present invention may include any fluid that may be used to prepare a suitable treatment fluid. Examples of suitable base fluids include, but are not limited to aqueous fluids, oleaginous fluids, and combinations thereof. Examples of suitable oleaginous fluids include, but are not limited to, olefins, internal olefins, alkanes, aromatic solvents, cycloalkanes, liquefied petroleum gas, kerosene, diesel oils, crude oils, heavy oils, gas oils, fuel oils, paraffin oils, mineral oils, low toxicity mineral oils, olefins, esters, amides, synthetic oils (e.g., polyolefins), polydiorganosiloxanes, siloxanes, organosiloxanes, ethers, acetals, dialkylcarbonates, hydrocarbons, diesel, crude oil, organic solvents, oil, and combinations thereof. Because the orthoester-based surfactants generally degrade with reduced pH, a treatment with an aqueous-base fluid should, in most embodiments, have a pH of about 8.5 or greater. Suitable aqueous liquids may include, but are not limited to, freshwater, seawater, saltwater, brines (e.g., natural or formulated brines), and combinations thereof. The aqueous liquid may be from any source, provided that it does not contain an excess of compounds that may adversely affect the emulsified treatment fluid. In some embodiments, non-aqueous fluids also may be used as the base fluid. In certain embodiments, the aqueous liquid may comprise a gelling agent (e.g., viscoelastic surfactants, natural or synthetic polymers, etc.) for gelling the aqueous liquid and increasing its viscosity, and, optionally, a crosslinking agent for crosslinking the gelling agent and further increasing the viscosity of the fluid.

The orthoester-based surfactants useful in the present invention generally may be any suitable orthoester-based surfactant. In certain embodiments, at least a portion of the orthoester-based surfactants are of Formula I:

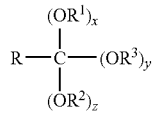

Formula I wherein R is hydrogen or an alkyl group having from 1 to 4 carbons, $R^1$ is a hydrophobic group, $R^2$ is a hydrophilic group, $R^3$ is $CH_3$, $C_2H_5$, $C_3H_7$, or $C_4H_9$, x is an integer from 1 to 2, y is an integer from 0 to 2, and z is an integer from 0 to 2, wherein the summation of x, y, and z is equal to 3. Preferably, $R^3$ is $CH_3$ or $C_2H_5$.

In certain embodiments, suitable orthoester-based surfactants may be synthesized from diketene acetals or multiketene acetals. In certain embodiments, suitable nonionic or cationic orthoester-based surfactants containing an amine may be synthesized by transesterification of an alkanolamine and a hydrophobic alcohol with a low molecular weight orthoester, or by the reaction of an alkanolamine and a hydrophobic alcohol with a diketene acetal or a multiketene acetal. Suitable orthoester-based surfactants and methods of synthesis are described in U.S. Pat. No. 6,653,395, the relevant disclosure of which is incorporated herein by reference. Other suitable orthoester-based surfactants and methods of synthesis are described in WO 03/018534 and United States PG Pub. No. 2004/0039235, the relevant disclosures of which are incorporated herein by reference.

The hydrophobic groups contained in the orthoester-based surfactants may be any hydrophobic groups derived from hydrophobic alcohols that are capable of undergoing a transesterification reaction with orthoesters. In certain embodiments, the hydrophobic groups may comprise monoalcohols derived from fatty alcohols, fatty alcohol ethoxylates, end-capped hydrophobic poly(alkylene oxides), poly(tetrahydrofuran), and polybutadiene hydroxyl terminated. Examples of suitable hydrophobic poly(alkylene oxides) include, for example, end-capped poly(butylene oxide), and end-capped poly(propylene oxide). Suitable hydrophobic groups include, for example, alkyl groups with 8 or more carbons. Suitable examples of alkyl groups with 8 or more carbons include, but are not limited to, 2-ethylhexyl, octyl, decyl, coco alkyl, lauryl, oleyl, rape seed alkyl, and tallow alkyl. Those of ordinary skill in the art, with the benefit of this disclosure, will be able to determine suitable hydrophobic groups based on, among other things, the hydrophilic-lipophilic balance and the particular function that the surfactant will perform.

The hydrophilic groups contained in the orthoester-based surfactants may be derived from hydrophilic alcohols. Suitable hydrophilic alcohols include, for example, end-capped poly(ethylene oxide) and alkanolamines. Examples of suitable alkanolamines include, but are not limited to, N,N-dimethylethanolamine; N,N-diethylethanolamine; N-methyldiethanolamine; N-methyl-hydroxyethylpiperazine; 1,4-bis(2-hydroxyethyl)piperazine; N,N-dimethyl-N',N'-bis(2-hydroxyethyl)propylenediamine; N,N-diethyl-N',N'-bis(2-hydroxyethyl)propylenediamine; 3-dimethylamino-1-propanol; 3-diethylamino-1-propanol; and triethanolamine. In certain embodiments, the hydrophilic groups may be derived from tertiary amines. Hydrophilic groups derived from tertiary amines may be suitable, in certain embodiments, because the tertiary amine may be less likely to cause undesired side reactions in the synthesis of the orthoester-based surfactant. In some embodiments, the orthoester-based surfactant containing tertiary amines may be quaternized by alkylation to form a quaternary ammonium compound a cationic orthoester-based surfactant.

In certain embodiments, suitable orthoester-based surfactants of Formula I may be synthesized by reacting, in one or more steps, a low molecular weight orthoester of Formula II, as illustrated below, with hydrophilic alcohols and hydrophobic alcohols in the presence of an acid catalyst:

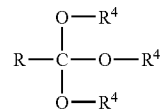

Formula II wherein R has the same meaning as from Formula I and $R^4$ is an alkyl group having from 1 to 6 carbons. Examples of suitable acid catalysts include methanesulphonic acid, p-toluenesulphonic acid, and citric acid. Examples of suitable low molecular weights orthoesters of Formula II include trimethyl orthoformate, trimethyl orthoacetate, triethyl orthoformate, triethyl orthoacetate, tripropyl orthoformate; and tripropyl orthoacetate. Low molecular weight orthoesters may be used due to the ease of transesterification undergone by these molecules with high molecular weight alcohols. Examples of suitable hydrophobic alcohols and hydrophilic alcohols are described above. In one embodiment, a suitable orthoester-based surfactant of Formula I may be synthesized by reacting trimethyl orthoformate with a mixture of hydrophilic and hydrophobic alcohols in the presence of an acid catalyst as illustrated in Reaction Scheme I:

Reaction Scheme I

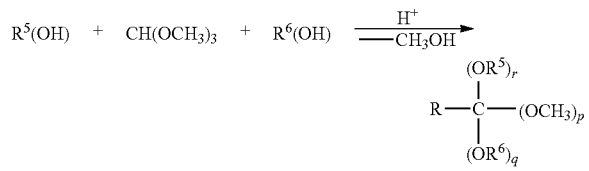

wherein R has the same meaning as from Formula I, $R^5$ is a hydrophobic group, $R^6$ is a hydrophilic group, r is an integer from 1 to 2, p is an integer from 0 to 2, and q is an integer from 0 to 2, wherein the summation of r, p, and q is equal to 3. Because the trimethyl orthoformate molecule has three positions that may be substituted by the reactants, the product of the reaction depicted in Reaction Scheme I is a mixture of several different reaction products. Some molecules will have one hydrophobic group substituent and one hydrophilic group substituent. Some molecules will have two hydrophobic group substituents. And some molecules will have two hydrophilic group substituents. The surface activity of the reaction products will depend, among other things, on the substituents, for example, molecules containing one hydrophobic group and one hydrophilic group in the same molecule should show surface activity. Generally, reaction products containing only the hydrophilic or the hydrophobic groups will show negligible to no surface activity.

In certain embodiments, suitable orthoester-based surfactants may be synthesized by reacting, in one or more steps, a diketene, or multiketene, acetal with one or more hydrophobic alcohols and one or more hydrophilic alcohols. Examples of suitable hydrophobic alcohols and hydrophilic alcohols that may be used in the synthesis of an orthoester-based surfactant from a diketene, or multiketene, acetal are described previously. Examples of suitable diketene, or multiketene, acetals may be synthesized as described in U.S. Pat. No. 4,304,767, the relevant disclosure of which is incorporated herein by reference. In one embodiment, as illustrated below in Reaction Scheme II, a diketene acetal may be synthesized by reacting pentaerythritol and chloroacetaldehyde dimethyl acetal in the presence of p-toluenesulfonic acid or methanesulfonic acid to afford 2 which on dehydrohalogenation in presence of t-butoxide in t-butanol afford diketene acetal 3, and a suitable orthoester-based surfactant 4 may be synthesized by reacting the resultant diketene acetal with one mole equivalent each of the hydrophobic and hydrophilic alcohols in the presence of a small amount of iodine dissolved in pyridine. In some embodiments, the orthoester-based surfactant may be synthesized by mixing the hydrophobic and hydrophilic alcohols with the diketene acetal without the aid of an iodine/pyridine catalyst, provided the alcohols and diketene acetals are extremely pure.

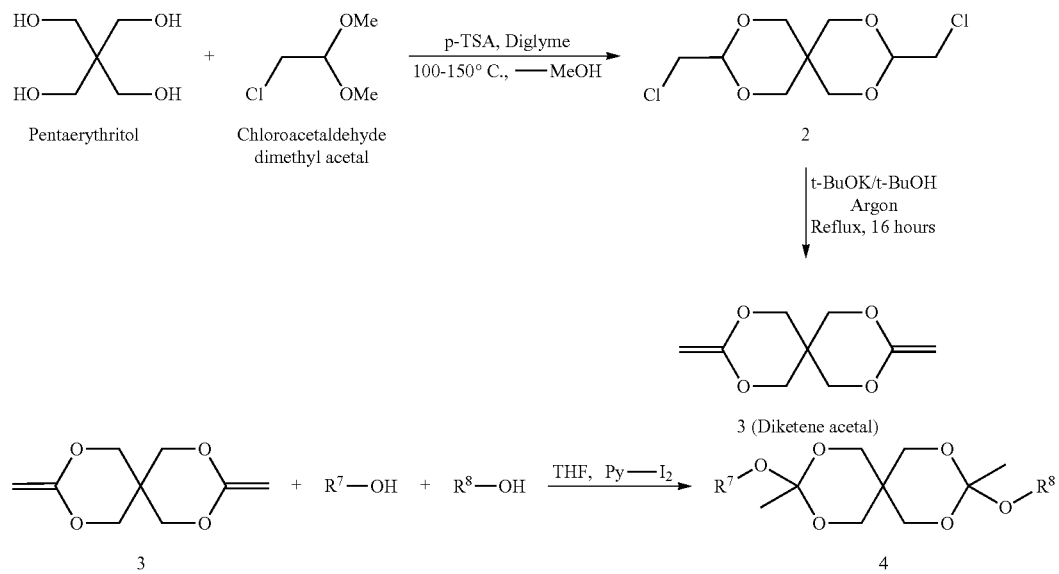

wherein $R^7$ is a hydrophobic group and $R^8$ is a hydrophilic group. As those of ordinary skill in the art will appreciate, the product of the reaction depicted in Reaction Scheme II is a mixture of several different reaction products. Some molecules will have one hydrophobic group substituent and one hydrophilic group substituent. Some molecules will have two hydrophobic group substituents. And some molecules will have two hydrophilic group substituents. The surface activity of the reaction products will depend, among other things, on the substituents, for example, molecules containing one hydrophobic group and one hydrophilic group in the same molecule should show surface activity. Generally, reaction products containing only the hydrophilic or the hydrophobic groups will show negligible to no surface activity.

In certain embodiments, a suitable orthoester-based surfactant containing an amine may be synthesized by transesterification reaction of an alkanolamine and a hydrophobic alcohol with a low molecular weight orthoester of the previously listed Formula II, or by reaction of an alkanolamine and a hydrophobic alcohol with a diketene acetal or a multiketene acetal. In certain embodiments, the orthoester-based surfactant containing an amine may be synthesized from a tertiary amine. In some embodiments, the orthoester-based surfactant containing a tertiary amine may be quaternized by alkylation to form a quaternary ammonium compound, for example, a cationic orthoester-based surfactant.

In some embodiments, the amine may be a tertiary amine or a quaternary ammonium salt. For example, a tertiary amine may be quarternized by reacting the orthoester-based surfactant containing a tertiary amine with an alkylating agent (e.g., methyl chloride or dimethylsulfate) to obtain a cationic orthoester-based surfactant. Suitable alkanolamines, low molecular weight orthoesters, and diketene acetals are described previously.

The particular function that the orthoester-based surfactants useful in the present invention will perform depends on a variety of factors. These factors may include, but are not limited to, the choice of hydrophobic and hydrophilic groups, the relative amounts of hydrophobic and hydrophilic groups and temperature. For example, whether an oil-in-water ("o/w") or a water-in-oil ("w/o") emulsion is formed may be determined by the relative hydrophobicity of the surfactant tail and the hydrophilicity of the head group. The hydrophilic/lipophilic balance ("HLB") of the surfactant may provide a quantitative prediction of whether the surfactant will facilitate the formation of an o/w or a w/o emulsion. The HLB may be determined from the chemical formula of the surfactant using empirically determined group numbers. Even the HLB method is only semi-empirical and other factors (such as the relative phase volumes of oil and water) may have a considerable influence on the type of emulsion formed.

By varying the above-listed factors, the specific properties of the orthoester-based surfactant such as solubility, wettability, emulsifying, foaming, defoaming, cloud point, gelling, detergency, and the like may be varied. For example, where used as an emulsifying agent, an orthoester-based surfactant having an HLB of from about 3 to about 6 may be suitable to stabilize a w/o emulsion. In other embodiments, for stabilizing an o/w emulsion, an orthoester-based surfactant having an HLB of from about 8 to about 18 may be suitable. Those of ordinary skill in the art, with the benefit of this disclosure, will be able to determine the appropriate orthoester-based surfactant to use for a particular application.

The amount of the orthoester-based surfactants useful in the present invention to include in the treatment fluids of the present invention will vary dependent upon, among other things, the particular application. In certain embodiments, the orthoester-based surfactants should be present in an amount in the range of from about 0.01% to about 5% by weight of the fluid. In certain embodiments, the orthoester-based surfactants should be present in an amount in the range of from about 0.05% to about 2% by weight of the fluid.

In some embodiments, where an aqueous-base fluid is used, the pH of the treatment fluids of the present invention may, among other things, affect the degradation of the orthoester-based surfactants. The orthoester-based surfactants useful in the present invention are generally stable at a pH of about 8.5 or greater. However, degradation of the orthoester linkage should generally result in destruction of the surface activity of the surfactants. At a pH of about 8 or less the orthoester-based surfactants should degrade at reasonable rates. Generally, a reduction in pH to neutral value (about pH 7) should allow the orthoester-based surfactant to degrade relatively quickly. The rates of degradation should increase with decreasing pH and increasing temperature. In subterranean applications, the buffering action of the formation together with temperature may, in some embodiments, provide the desired degradation of the orthoester-based surfactant. Generally, the pH of a particular treatment fluid of the present invention may be maintained at about 8.5 or greater. In the embodiments where a nonaqueous base fluid is used, the orthoester-based surfactant present in the treatment fluid should begin to degrade upon interaction with formation fluids (e.g., formation brines).

To maintain the pH of the treatment fluids of the present invention in a desired range if necessary, the fluids optionally may comprise a pH buffer and/or a strong base. The pH buffer and/or strong base may be included in the treatment fluids to adjust pH to, and/or maintain pH in, a desired range, among other things, for the stability of the orthoester-based degradable surfactants. In some embodiments, a pH buffer may be used, for example, where an acid will be used to lower the pH of the treatment fluid at a desired time. Examples of suitable pH buffers include, but are not limited to, sodium carbonate, potassium carbonate, sodium or potassium diacetate, sodium or potassium phosphate, sodium or potassium hydrogen phosphate, and combinations thereof. In some embodiments, a strong base may be used, for example, where the formation buffering effect will be used to lower the pH of the treatment fluid. Examples of suitable strong bases include, but are not limited to, sodium hydroxide, potassium hydroxide, and combinations thereof. The pH buffer and/or strong base may be present in the treatment fluids of the present invention in an amount sufficient to maintain the pH of the treatment fluid at or above about 8.5 as desired. One of ordinary skill in the art, with the benefit of this disclosure, will recognize the appropriate pH buffer and/or strong base and amount thereof to use for a chosen application.

While the orthoester-based surfactants included in the treatment fluids of the present invention are generally degradable, or cleavable, it may be desired, in some embodiments, for a faster degradation. Therefore, in some embodiments, to facilitate the degradation of the orthoester-based surfactants and thus generally destroy or reduce their surface activity, the pH of the treatment fluid may be decreased at a desired time. Generally, at a pH of about 8 or less the orthoester-based surfactants should degrade at reasonable rates. In subterranean applications, the buffering action of the formation together with temperature may, in some embodiments, provide the desired degradation. In some embodiments, the orthoester-based surfactants may be included in the treatment fluid to facilitate the formation of an emulsion. At a desired time, the emulsion may be broken by decreasing the pH of the treatment fluid's aqueous phase sufficiently to allow for the degradation of the orthoester-based surfactant. Upon degradation of the orthoester linkages, the reduction in surface activity of the orthoester-based surfactant will facilitate a break of the emulsion. Separation of the two phases of an emulsion is commonly referred to as "breaking" the emulsion.

To reduce the pH of the treatment fluid at a desired time a number of methods may be employed. In some embodiments, the treatment fluid may be contacted by an acid after introduction of the treatment fluid into the subterranean formation. Examples of suitable acids include, but are not limited to, hydrochloric acid, hydrofluoric acid, formic acid, phosphoric acid, sulfamic acid, acetic acid, derivatives thereof, and mixtures thereof.

In other embodiments a delayed-release acid, such as an acid-releasing degradable material or an encapsulated acid, may be included in the treatment fluid so as to reduce the pH of the treatment fluid at a desired time, for example, after introduction of the treatment fluid into the subterranean formation. Suitable encapsulated acids that may be included in the treatment fluids of the present invention include but are not limited to, fumaric acid, formic acid, acetic acid, acetic anhydride, anhydrides, hydrochloric acid, hydrofluoric acid, hydroxyfluoboric acid, combinations thereof, and the like. Exemplary encapsulation methodology is described in U.S. Pat. Nos. 5,373,901; 6,444,316; 6,527,051; and 6,554,071, the relevant disclosures of which are incorporated herein by reference. Acid-releasing degradable materials also may be included in the treatment fluids of the present invention to decrease the pH of the fluid. Suitable acid-releasing degradable materials that may be used in conjunction with the present invention are those materials that are substantially water insoluble such that they degrade over time, rather than instantaneously, in an aqueous environment to produce an acid. Examples of suitable acid-releasing degradable materials include esters, polyesters, orthoesters, polyorthoesters, lactides, polylactides, glycolides, polyglycolides, substituted lactides wherein the substituted group comprises hydrogen, alkyl, aryl, alkylaryl, acetyl heteroatoms and mixtures thereof, substantially water insoluble anhydrides, poly(anhydrides), and mixtures and copolymers thereof. Materials suitable for use as an acid-releasing degradable material of the present invention may be considered degradable if the degradation is due, inter alia, to chemical processes, such as hydrolysis, oxidation, or enzymatic decomposition. The appropriate pH-adjusting agent or acid-releasing material and amount thereof may depend upon the formation characteristics and conditions, the particular orthoester-based surfactant chosen, and other factors known to individuals skilled in the art, with the benefit of this disclosure.

Depending on the particular application, the treatment fluids of the present invention may further comprise any of a variety of additional additives. Examples of suitable additives include, but are not limited to, proppant particulates, gravel particulates, weighting agents, organophilic clays, bridging agents, fluid loss control agents, wetting agents, corrosion inhibitors, scale inhibitors, fluid loss control additives, gas, paraffin inhibitors, asphaltene inhibitors, catalysts, hydrate inhibitors, iron control agents, clay control agents, biocides, friction reducers, combinations thereof and the like. The particular additives included in the treatment fluids should not adversely affect other components of the treatment fluid or the orthoester-based surfactant. Individuals skilled in the art, with the benefit of this disclosure, will recognize the types of additives to include for a particular application.

The treatment fluids of the present invention may be used in any suitable subterranean application. Such applications may include, but are not limited to, drilling operations, stimulation treatments (e.g., fracturing treatments), and completion operations (e.g., sand control treatments, gravel packing). An example method of the present invention comprises: providing a treatment fluid of the present invention that comprises a base fluid and an orthoester-based surfactant, introducing the treatment fluid into a subterranean formation. Introducing the treatment fluid into the subterranean fluid may include introduction of the treatment fluid into a well bore that penetrates the subterranean formation. In some embodiments, the method may further comprise allowing at least a portion of the orthoester-based surfactant to degrade. As previously discussed, at a desired time, the pH of the treatment fluid may be reduced so as to facilitate the degradation of the orthoester-based surfactant, thereby destroying or reducing the surface activity of the surfactant.

In the drilling embodiments, the treatment fluids may be used in drilling at least a portion of a well bore that penetrates the subterranean formation. For example, the treatment fluids may be used as a drilling fluid or a drill-in fluid. In another embodiment, the treatment fluids of the present invention may be used in a sand control treatment (e.g., as a gravel-packing fluid). In the sand control embodiments, the treatment fluids may further comprise gravel particulates, wherein at least a portion of the gravel particulates may be deposited within or adjacent to a portion of the subterranean formation to form a gravel pack. As referred to herein, the term "gravel pack" refers to gravel particulates that have been deposited in a well bore so as to provide at least some degree of sand control, such as by packing the annulus between the well bore and a screen disposed in the well bore with the gravel particulates of a specific size designed to prevent the passage of formation sand. In some embodiments, screenless gravel packs also may be employed. In the fracturing embodiments, the treatment fluid may be introduced into the subterranean formation at or above pressure sufficient to create or enhance one or more fractures in the subterranean formation.

II. Emulsified Embodiments of the Treatment Fluids of the Present Invention

For the emulsion embodiments, the treatment fluids of the present invention may be an emulsified treatment fluid that comprises an oleaginous phase, an aqueous phase having a pH of about 8.5 or greater, and an orthoester-based surfactant. As referred to herein, the term "emulsified treatment fluid" refers to any emulsified fluid that has a continuous phase and a discontinuous phase, whether a w/o emulsion or an o/w emulsion. In an o/w emulsion, the aqueous phase is the continuous (or external) phase and the oleaginous phase is the discontinuous (or internal) phase. In a w/o emulsion (or invert emulsion), the aqueous phase is the discontinuous phase and the oleaginous phase is the continuous phase.

Generally, the emulsified treatment fluids of the present invention are suitable for use in a variety of applications where an o/w emulsion or a w/o emulsion is suitable. For example, the orthoester-based surfactants may be useful for facilitating the formation of w/o emulsions that may be used in a variety of subterranean operations including, drilling operations (e.g., as a drilling fluid or a drill-in fluid), fracturing treatment (e.g., as a fracturing fluid), well bore cleanups, viscous sweeps, and sand control treatments (e.g., as a gravel-packing fluid). A drill-in fluid is a drilling fluid formulated for drilling the reservoir portion of the subterranean formation. Also, the orthoester-based surfactants may be useful for facilitating the formation of an o/w emulsion that may be used in a variety of subterranean applications, including well bore cleanups, such as for the removal of paraffin, asphaltene, and/or scale deposits. In another embodiment, the orthoester-based surfactant may be used to form an emulsified treatment fluid that may be used to facilitate the transport of the oleaginous phase, for example, to facilitate the flow of heavy oil through a pipeline. As used herein, the term "heavy oil" refers to any petroleum with an API gravity of less than 28 degrees or a high specific density.

The oleaginous phase of the emulsified treatment fluids of the present invention may comprise any oleaginous fluid suitable for use in emulsions used in subterranean applications. The oleaginous fluid may be from natural or synthetic sources. Examples of suitable oleaginous fluids include, but are not limited to, α-olefins, internal olefins, alkanes, aromatic solvents, cycloalkanes, liquefied petroleum gas, kerosene, diesel oils, crude oils, heavy oils, gas oils, fuel oils, paraffin oils, mineral oils, low toxicity mineral oils, olefins, esters, amides, synthetic oils (e.g., polyolefins), polydiorganosiloxanes, siloxanes, organosiloxanes, ethers, acetals, dialkylcarbonates, hydrocarbons, and combinations thereof.

The amount of the oleaginous phase to include in the emulsified treatment fluid depends on a number of factors, including the particular orthoester-based surfactant used, the type of emulsion (e.g., o/w or w/o), the desired application, and rheology. For example, in certain embodiments, such as stimulation, the emulsified treatment fluid should have sufficient viscosity for proppant transport. In some embodiments, for an o/w emulsion, the oleaginous phase may be present in an amount in the range of from about 10% to about 65% by volume of the emulsified treatment fluid. In some embodiments, for a w/o emulsion, the oleaginous phase may be present in an amount in the range of from about 20% to about 90% by volume of the emulsified treatment fluid.

For the emulsion embodiments, the emulsified treatment fluids of the present invention may also comprise an aqueous phase. Generally, the aqueous phase may comprise an aqueous liquid. Suitable aqueous liquids may include, but are not limited to, freshwater, seawater, saltwater, brines (e.g., natural or formulated brines), and combinations thereof. The aqueous liquid may be from any source, provided that it does not contain an excess of compounds that may adversely affect the emulsified treatment fluid.

The amount of the aqueous phase to include in the emulsified treatment fluid depends on a number of factors, including the particular orthoester-based surfactant used, the type of emulsion (e.g., o/w or w/o), the desired application, and rheology. In some embodiments, for an o/w emulsion, the aqueous phase may be present in an amount in the range of from about 35% to about 90% by volume of the emulsified treatment fluid. In some embodiments, for a w/o emulsion, the aqueous phase generally may be present in an amount in the range of from about 10% to about by 80% volume of the emulsified treatment fluid.

Generally, the orthoester-based surfactant should be included in the emulsified treatment fluids of the present invention so as to reduce the surface tension between the oleaginous phase and the aqueous phase so as to facilitate the formation and stabilization of the emulsified treatment fluids of the present invention. As discussed previously, the orthoester-based surfactant may be tailored so as to facilitate the formation of an o/w or a w/o emulsion. The orthoester-based surfactant may be present in the emulsified treatment fluids of the present invention in amount in the range of from about 0.01% to about 5% by weight of the emulsified treatment fluids. In another embodiment, the orthoester-based surfactant may be present in the emulsified treatment fluids of the present invention in an amount in the range of from about 1% to about 3% by weight of the emulsified treatment fluids.

As previously discussed, the orthoester-based surfactants included in the emulsified treatment fluids of the present invention are generally stable at a pH of about 8.5 or greater. As a result, for stabilization of the orthoester-based surfactants, the aqueous phase of the emulsified treatment fluids of the present invention should have a pH of about 8.5 or greater. To maintain the pH of the treatment fluids of the present invention in a desired range, the aqueous phase optionally may comprise a pH buffer and/or a strong base. The pH buffer and/or strong base may be included in the aqueous phase to adjust the pH, and/or maintain the pH in, a desired range, among other things, for the stability of the orthoester-based degradable surfactants. In some embodiments, a pH buffer may be used, for example, where an acid will be used to lower the pH of the treatment fluid at a desired time. In some embodiments, a strong base may be used, for example, where the formation buffering effect will be used to lower the pH of the treatment fluid. Suitable pH buffers and strong bases may include those described previously. The pH buffer and/or strong base may be present in the aqueous phase of the present invention in an amount sufficient to maintain the pH of the treatment fluid at or above about 8.5 as desired. One of ordinary skill in the art, with the benefit of this disclosure, will recognize the appropriate pH buffer and/or strong base and amount thereof buffer to use for a chosen application.

Because the orthoester-based surfactants act to stabilize the emulsified treatment fluids of the present invention, the emulsified treatment fluids should have a delayed break, due to the degradation of the surfactants therein, without the need for inclusion of conventional emulsion breakers (e.g., acid precursors) therein. In subterranean applications, the buffering action of the formation together with temperature may, in some embodiments, provide the desired degradation. However, in some embodiments, a faster break may be desired so that a delayed-release acid, such as an acid-releasing degradable material or an encapsulated acid, may be included in the emulsified treatment fluids. Suitable delayed-release acids may include those described previously. In some embodiments, the emulsified treatment fluids of the present invention may be contacted by an acid after introduction of the emulsified treatment fluid into the well bore. Examples of suitable acids include, but are not limited to, hydrochloric acid, hydrofluoric acid, formic acid, phosphoric acid, sulfamic acid, acetic acid, derivatives thereof, and mixtures thereof.

Depending on the particular application, the emulsified treatment fluids of the present invention may further comprise any of a variety of additional additives. Examples of suitable additives include, but are not limited to, proppant particulates, gravel particulates, weighting agents, organophilic clays, bridging agents, fluid loss control agents, wetting agents, corrosion inhibitors, scale inhibitors, fluid loss control additives, gas, paraffin inhibitors, asphaltene inhibitors, catalysts, hydrate inhibitors, iron control agents, clay control agents, biocides, friction reducers, combinations thereof, and the like. The particular additives included in the treatment fluids should not adversely affect other components of the emulsified treatment fluid. Individuals skilled in the art, with the benefit of this disclosure, will recognize the types of additives to include for a particular application.

The emulsified treatment fluids of the present invention may be used in any suitable subterranean application where an emulsion may be used, including, but not limited to, drilling operations (e.g., as a drilling fluid or a drill-in fluid), fracturing treatment (e.g., as a fracturing fluid), well bore cleanups, viscous sweeps, and sand control treatments (e.g., as a gravel-packing fluid). An example method of the present invention comprises: providing an emulsified treatment fluids of the present invention that comprises an orthoester-based surfactant, an oleaginous phase, and an aqueous phase having a pH of about 8.5 or greater; and introducing the emulsified treatment fluid into a subterranean formation. Introducing the emulsified treatment fluid into the subterranean formation includes introducing the emulsified treatment fluid into a well bore that penetrates the subterranean formation. As previously discussed, the emulsified treatment fluid may be an o/w or a w/o emulsion.

In the drilling embodiments, the emulsified treatment fluids may be used in drilling at least a portion of a well bore that penetrates the subterranean formation. For example, the emulsified treatment fluids may be used as a drilling fluid or a drill-in fluid. In another embodiment, the emulsified treatment fluids of the present invention may be used in a sand control treatment (e.g., as a gravel-packing fluid). In the sand control embodiments, the emulsified treatment fluids may further comprise gravel particulates, wherein at least a portion of the gravel particulates may be deposited within or adjacent to a portion of the subterranean formation to form a gravel pack. In the fracturing embodiments, the emulsified treatment fluid may be introduced into the subterranean formation at or above pressure sufficient to create or enhance one or more fractures in the subterranean formation.

Another example of a method of the present invention comprises utilizing the emulsified treatment fluids of the present invention to facilitate the flow of the oleaginous phase through a conduit, for example, to facilitate the flow of heavy oil through a pipeline. An example of such a method may comprise: providing an emulsified treatment fluid of the present invention that comprises an orthoester-based surfactant, an oleaginous phase, and an aqueous phase having a pH of about 8.5 or greater; flowing the emulsified treatment fluid through a conduit; reducing the pH of the aqueous phase so as to facilitate degradation of at least a portion of the orthoester-based surfactant, thereby facilitating the separation of the oleaginous phase and the aqueous phase. Since the emulsified treatment fluid may be broken by degradation of the orthoester-based surfactant, when the pH of the aqueous phase is reduced, the oleaginous phase and the aqueous phase should separate. Among other things, this may allow for recovery of the oleaginous fluid at a desired location. In most embodiments, the pH of the aqueous phase may reduced at the receiving end of the pipeline where desired to recover the oleaginous fluid. In certain embodiments, the oleaginous phase may be a heavy oil. Where a heavy oil is used, the emulsified treatment fluid may be used to facilitate the flow of the heavy through a conduit, such as a pipeline.

To facilitate a better understanding of the present invention, the following examples of preferred embodiments are given. In no way should the following examples be read to limit, or define, the scope of the invention.

EXAMPLE 1

A 75/25 o/w emulsion was prepared in accordance with the following procedure. First, 2 grams (g) of an orthoester-based surfactant in accordance with Formula I ($R^1$=octadecyl, $R^2$=MPEG-350, and $R^3$=$CH_3$) were dissolved in 50 milliliters (mL) of a solution comprising 0.05% sodium hydroxide by weight of the solution. To the resulting solution, 150 mL of mineral oil (HDF-2000) were added while shearing in a blender to form an o/w emulsion. The rheology of the o/w emulsion prepared in accordance with the above procedure was measured on a FANN® 35 viscometer fitted with a yield stress adapter. Yield stress adapters are described in U.S. Pat. No. 6,874,353, the relevant disclosure of which is incorporated herein by reference. Data analysis was done with the Casson model to determine that: yield stress=13 Pascals; infinite shear rate viscosity=97 centipoise; and $r^2$=0.99, wherein r is the correlation coefficient.

EXAMPLE 2

A 75/25 w/o emulsion was prepared in accordance with the following procedure. First, 4 g of an orthoester-based surfactant in accordance with Formula I ($R^1$=butyl capped PPO-2500, $R^2$=MPEG-350, and $R^3$=$CH_3$) were dissolved in 50 mL of a mineral oil (HDF-2000) containing 10% of ACCOLADE™ drilling fluid base oil by volume. ACCOLADE™ drilling fluid base oil is commercially available from Halliburton Energy Services, Inc., Duncan Okla. To the resulting solution, 150 mL of water were added while shearing in a blender to form a w/o emulsion. The rheology of the w/o emulsion prepared in accordance with the above procedure was measured on a FANN® 35 viscometer fitted with a yield stress adapter. Yield stress adapters are described in U.S. Pat. No. 6,874,353, the relevant disclosure of which is incorporated herein by reference. Data analysis was done with the Casson model to determine that: yield stress=40 Pascals; infinite shear rate viscosity=153 centipoise; and $r^2$=0.99, wherein r is the correlation coefficient.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee.

What is claimed is:

1. A composition comprising a base fluid, particulates selected from the group consisting of gravel particulates and proppant particulates, and from about 0.01% to about 5% by weight of an orthoester-based surfactant wherein at least a portion of the orthoester-based surfactant is of the following formula:

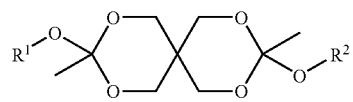

wherein $R^1$ is a hydrophobic group and wherein the surfactant is not a solid and $R^2$ is a hydrophilic group.

2. The composition of claim 1 wherein the orthoester-based surfactant comprises more than one degradable orthoester linkage.

3. The composition of claim 1 wherein the base fluid has a pH of about 8.5 or greater.

4. The composition of claim 1 wherein the base fluid comprises at least one fluid selected from the group consisting of: an aqueous fluid, an oleaginous fluid, and any combination thereof.

5. The composition of claim 1 wherein the orthoester-based surfactant is an emulsifying agent, a non-emulsifying agent, a foaming agent, a defoaming agent, a dispersant, a wetting agent, or any combination thereof.

6. The composition of claim 1 wherein the orthoester-based surfactant is synthesized from a diketene acetal or a multiketene acetal by the addition of a hydrophobic alcohol and a hydrophilic alcohol.

7. The composition of claim 1 wherein the orthoester-based surfactant contains an amine and is synthesized by reaction of an alkanolamine and a hydrophobic alcohol with a diketene acetal or a multiketene acetal, or by transesterification of an alkanolamine and a hydrophobic alcohol with a low molecular weight orthoester of the following formula:

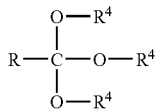

wherein R is hydrogen or an alkyl group having from 1 to 4 carbons, and $R^4$ is an alkyl group having from 1 to 6 carbons.

8. The composition of claim 1 of wherein the orthoester-based surfactant comprises a tertiary amine.

9. The composition of claim 1 wherein the hydrophobic group comprises at least one hydrophobic group selected from the group consisting of: a fatty alcohol, a fatty alcohol ethoxylate, an end-capped hydrophobic poly(alkylene oxide), poly(tetrahydrofuran), polybutadiene hydroxyl terminated; and any combination thereof.

10. The composition of claim 1 wherein the hydrophobic group comprises at least one alkyl group with 8 or more carbons.

11. The composition of claim 1 wherein the hydrophilic group is derived from a hydrophilic alcohol selected from the group consisting of: an end-capped poly(ethylene oxide), an alkanolamine, and any combination thereof.

12. The composition of claim 5 wherein the hydrophobic group is derived from an end-capped hydrophobic poly(alkylene oxide), and the hydrophilic group is synthesized from end-capped poly(ethylene oxide).

13. The composition of claim 1 further comprising at least one additive selected from the group consisting of: a pH buffer; a strong base; an acid-releasing degradable material; an encapsulated acid; and any combination thereof.

14. An emulsified composition comprising an oleaginous phase, an aqueous phase having a pH of about 8.5 or greater, particulates selected from the group consisting of gravel particulates and proppant particulates, and from about 0.01% to about 5% by weight of an orthoester-based surfactant wherein at least a portion of the orthoester-based surfactant is of the following formula:

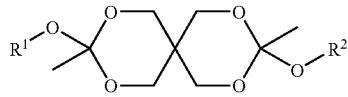

wherein $R^1$ is a hydrophobic group and $R^2$ is a hydrophilic group and wherein the surfactant is not a solid.

15. The emulsified composition of claim 14 wherein the oleaginous phase comprises a heavy oil.

16. The emulsified composition of claim 14 wherein the orthoester-based surfactant is synthesized from a diketene acetal or a multiketene acetal by the addition of a hydrophobic alcohol and a hydrophilic alcohol.

17. The emulsified composition of claim 14 wherein the orthoester-based surfactant contains an amine and is synthesized by reaction of an alkanolamine and a hydrophobic alcohol with a diketene acetal or a multiketene acetal, or by transesterification of an alkanolamine and a hydrophobic alcohol with a low molecular weight orthoester of the following formula:

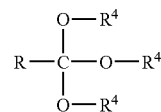

wherein R is hydrogen or an alkyl group having from 1 to 4 carbons, and $R^4$ is an alkyl group having from 1 to 6 carbons.

18. A composition comprising particulates selected from the group consisting of gravel particulates and proppant particulates and from about 0.01% to about 5% by weight of an orthoester-based surfactant synthesized from a diketene acetal or a multiketene acetal by the addition of one or more hydrophobic alcohols and one or more hydrophilic alcohols wherein at least a portion of the orthoester-based surfactant is of the following formula:

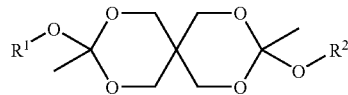

wherein $R^1$ is a hydrophobic group and $R^2$ is a hydrophilic group and wherein the surfactant is not a solid.

\* \* \* \* \*